United States Patent [19]

Little et al.

[11] 4,139,003

[45] * Feb. 13, 1979

[54] WATERPROOF CAST PROTECTOR

[76] Inventors: John D. Little, 25097 Champlain Rd., Laguna Hills, Calif. 92653; James Z. Cloud, Jr., 25839 Marguerite Pkway., Apt. 103, Mission Viejo, Calif. 92675

[*] Notice: The portion of the term of this patent subsequent to Aug. 23, 1994, has been disclaimed.

[21] Appl. No.: 784,496

[22] Filed: Apr. 4, 1977

Related U.S. Application Data

[62] Division of Ser. No. 636,508, Dec. 1, 1975, Pat. No. 4,043,326.

[51] Int. Cl.² .............................................. A61F 13/00
[52] U.S. Cl. ...................................... 128/82; 128/157
[58] Field of Search ................ 128/82, 132, 157, 165, 128/171; 2/21

[56]  References Cited

U.S. PATENT DOCUMENTS

| 835,806 | 11/1906 | Witten | 128/157 |
|---|---|---|---|
| 2,244,871 | 6/1941 | Guinzburg | 128/82 X |
| 3,018,484 | 1/1962 | Koehn | 2/21 |
| 3,659,599 | 5/1972 | McLaughlin | 128/157 |

*Primary Examiner*—John D. Yasko
*Attorney, Agent, or Firm*—Knobbe, Martens, Olson, Hubbard & Bear

[57]  ABSTRACT

A flexible covering for placement over an individual's injured limb having a cast or bandage. The covering has a receptacle portion and a sealing portion which are designed respectively to receive the foot or hand of the limb and the leg or arm portion of the limb. The covering is designed for use by the individual with the injured limb when he is bathing in order to protect the cast or bandaged area from contact with water. The sealing portion has an interior diameter smaller than the diameter of the limb above the cast or bandage in order to provide a sealing engagement with the limb.

4 Claims, 6 Drawing Figures

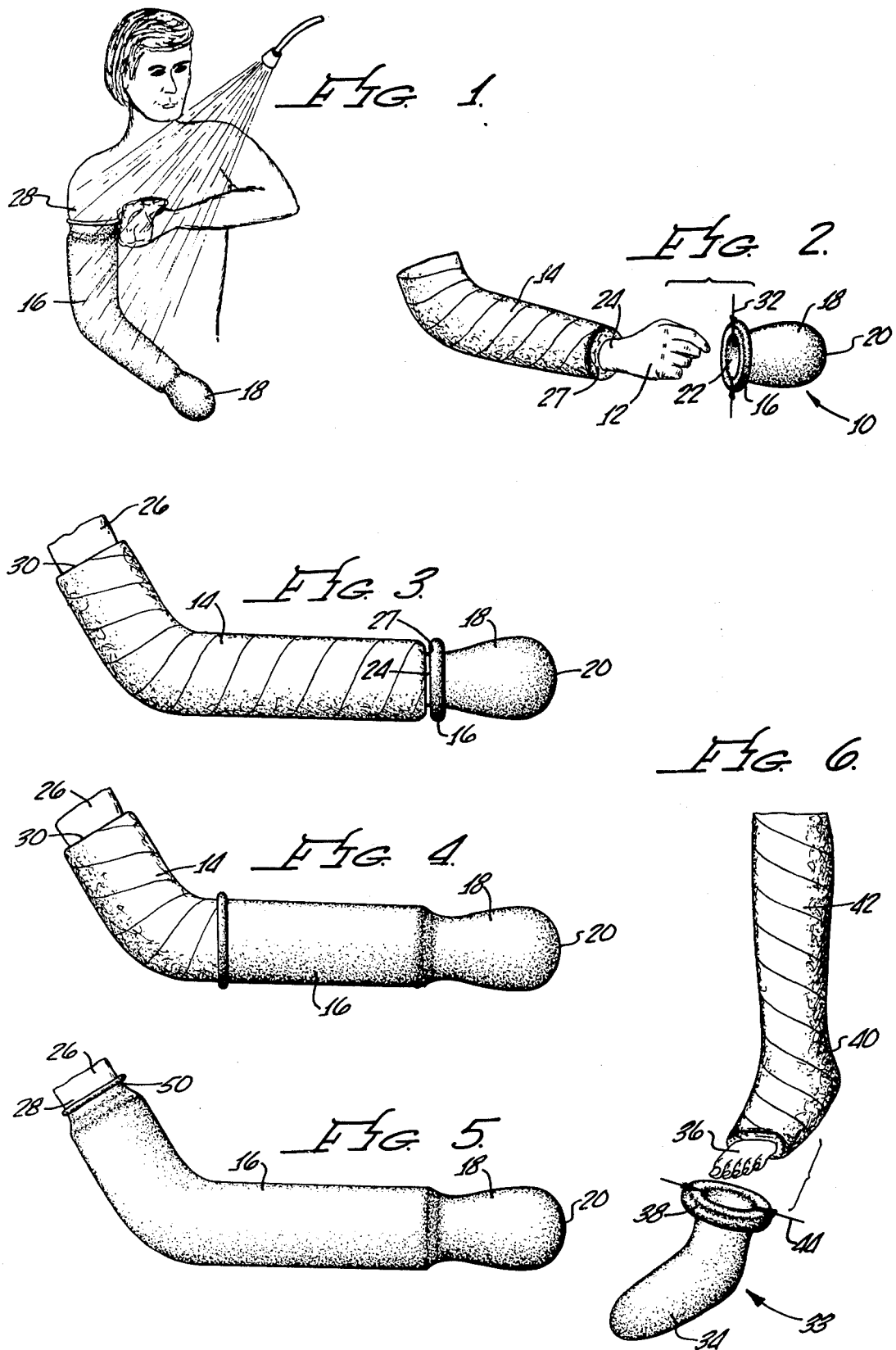

WATERPROOF CAST PROTECTOR

This is a division of Ser. No. 636,508 filed Dec. 1, 1975, now U.S. Pat. No. 4,043,326.

BACKGROUND OF THE INVENTION

This invention relates to the field of protective coverings for injured areas of an individual and more specifically relates to a covering which is designed to provide a protection to the cast or bandage area of the limb while the individual is bathing. One of the most frustrating situations for an individual who has a cast on either his arm or leg is the inability to bathe normally using a shower or bath because of the danger of water damage to the cast or bandaged area. Consequently, the individual is forced to utilize a so-called sponge bath which is more time-consuming and more inconvenient, rendering a less than adequate job of cleansing.

In the prior art, the typical approach of an individual who desires to take a shower with a cast is to place a plastic type bag over his leg or arm and to secure by tying it or placing a rubber band around the upper portion of it above the cast. Although this sometimes provides the satisfactory sealing, the seal in most instances is not proper and will result in some moisture entering the cast area. Furthermore, an individual who has one arm in a cast does not have the dexterity to adequately tie or seal the upper portion of the bag over the top of the cast on the opposite arm. Typically waterproof protectors used for patients having a cast when bathing have been the homemade type which are generally inadequate for sealing moisture from the cast, and also require the aid of a second individual to help in the placement of the covering over the cast.

SUMMARY OF THE INVENTION

This invention is comprised of a unitary flexible covering having a receptacle portion and a sealing portion. The receptacle portion has a closed end and an open end, the latter of which receives the foot or hand. Formed around the opening is a ridge or rib which contains the sealing portion that is rolled up on itself. Once the hand or foot is within the receptacle portion, the sealing portion is unrolled along the cast to a position on the limb above the upper portion of the cast. The sealing portion in an arm covering is smaller in cross-sectional area than the receptacle portion, and the sealing portion of both an arm and leg covering is smaller in diameter than the typical diameter of an individual's limb at the sealing position. Consequently, as the sealing portion is rolled up the cast it provides a tight seal over the cast and, when in contact with the skin of the individual on the limb above the cast, maintains a tight seal to prevent the entrance of any water into the cast area.

The covering device is designed to allow easy application by the temporarily handicapped individual, often eliminating the need for additional help when placing the covering over the cast, since on an arm cast covering for example he can easily apply the covering by the use of his free arm. The device is designed to be disposable after use and can be easily removed by simply rolling the sealing portion down the cast area to a position adjacent the wrist or ankle of the individual where the receptacle portion can be removed from the hand or foot. Also, the device may be simply cut with scissors for easy removal.

This invention provides an individual with a covering device that is inexpensive and easy to apply, allowing the individual to maintain his ability to bathe in a normal fashion and alleviating much of the inconvenience associated with having a cast or a heavily bandaged arm or leg.

BRIEF DESCRIPTION OF THE DRAWINGS

FIG. 1 shows the use of the invention by an individual while he is bathing;

FIG. 2 is a perspective view of the invention prior to application to an arm having a cast;

FIG. 3 shows the individual's hand inserted within the receptacle portion of the invention;

FIG. 4 shows the sealing portion of the invention having been unrolled partially up the individual's cast;

FIG. 5 shows the covering completely over the cast with the sealing engagement of the covering with the individual's arm; and FIG. 6 shows a perspective view of the embodiment of the invention for use on an individual's foot and leg cast.

DETAILED DESCRIPTION OF THE INVENTION

Referring to FIG. 2, the arm embodiment of the invention is shown generally at 10 in its preuse configuration ready for placement over the hand 12 and arm cast 14. The protective covering 10 is comprised of a sealing or adjustable portion 16 and a receptacle or bag portion 18. The receptacle portion has a closed end 20 and an open end 22 which is designed to receive the hand or lower manipulative joints 12. The interior of the receptacle portion 18 is designed to comfortably cover the hand 12.

With respect to FIGS. 2 and 3, the receptacle or receiving portion 18 is shown covering the hand with the sealing portion 16 surrounding the wrist 24 of the individual's arm 26. The sealing portion 16 is a rib of covering material which has been formed by rolling the generally tubular shaped material over itself down to the receptacle portion 18 forming the opening 22. Once the hand 12 is covered by the receptacle portion 18, the sealing portion 16 is unrolled onto the cast 14 over the end 27 closest to the hand, as shown in FIG. 4. The sealing portion is continually unrolled until it reaches a position 28 on the individual's arm 26 above the upper end or edge 30 of the cast 14 furthest from the hand as shown in FIGS. 4 and 5.

With respect to FIG. 2 the relaxed diameter 32 of the interior of the sealing portion 16 is smaller than the general diameter of the individual's arm, so that when the sealing portion 16 is positioned on the individual's arm 26 at the position 28 in FIG. 5 above the cast 14, the flexible and resilient material from which the covering is made will provide a watertight seal to protect the enclosed cast from contact with moisture.

With respect to FIG. 6 the leg embodiment 33 of this invention is shown with a receptacle portion 34 designed to easily receive the cast-covered foot area 36 of the individual. Integrally connected to the receptacle or receiving portion 34 is the sealing portion 38 which becomes positioned adjacent the ankle area 40 of the individual when the foot or lower manipulative joints are placed within the receptacle 34. As with the arm embodiment 10 of the invention the sealing portion 38 of the leg embodiment 33 of the invention is rolled over the leg cast 42 up to the position above the upper edge of the cast and seals against the skin of the patient's leg to provide a waterproof seal against the introduction of moisture to the cast or bandage. Similarly, the interior diameter 44 of the sealing portion 38 in the relaxed position is smaller than the diameter of the patient's typical leg. It must be noted that in the manufacturing of the present invention various sized coverings will be made to accommodate children of different ages as well as adults of different sizes.

Turning briefly to the general use and operation of the invention with respect to the arm embodiment 10, the individual will utilize his good arm to hold the covering device 10 and insert the hand 12 of his injured arm into the receptacle portion 18 as shown in FIG. 3. When the sealing portion 16 is adjacent his wrist 24, it is unrolled up over the edge 27 of the cast 14 up to a position 28 in FIG. 5 above the cast onto the patient's skin to provide a tight waterproof seal. The individual can then enter a shower or bath and bathe himself without causing any water damage to his cast or bandaged arm. When the use of the waterproof covering is completed, the individual simply rolls the sealing portion 16 back down the cast to a position adjacent his wrist 24 and then slips the receptacle portion 18 off his hand. The operation is the same for the leg and foot embodiment 33 with the receptacle portion 34 designed to receive the foot 36 and, when the sealing portion 38 is placed adjacent the ankle 40, it is then unrolled up over the cast to a point above the edge of the upper portion of the cast. The reverse operation is carried out to remove the covering once the bathing has been completed.

It should be noted that it would be possible to design the protective covering to be of a single tubular shape being completely rolled down to its closed end, so that the hand and fingers are placed adjacent the closed end and the sealing portion is then rolled over both the hand and the arm. This could prove to be a satisfactory waterproof seal for the cast depending upon the type of the resilient material that is used. However, the preferred embodiments include a receptacle portion which has a larger interior area than the sealing portion in order to provide easier covering of the hand or the foot. When either the hand or foot are covered with a cast, making them quite large, the covering would otherwise tend to stretch and possibly permanently deform the sealing portion of the covering, destroying the resilient sealing function of the sealing portion before it is placed completely up the arm.

When the arm covering 10 is completely unrolled as shown in FIG. 5, the sealing portion 16 has a solid resilient ring 50 which contacts the arm 26 adjacent the position 28. The relaxed diameter of the ring 50 is smaller than the diameter of the individual's limb at the sealing position such as at position 28 on the arm 26 in FIG. 5. This ring 50 enhances a tight seal against the arm 26 to prevent the contact of any moisture with the cast 14. In addition, the ring 50 facilitates the individual's ability to initiate rolling the covering down off the cast when he has finished bathing. A similar ring (not shown) is incorporated in the leg embodiment 33 of the waterproof covering.

What is claimed is:

1. A unitary, flexible covering to seal a cast on an individual's arm or leg and adapted to accommodate limbs and casts of a considerable range of lengths, comprising:

an elongate tube of resilient material for receiving said arm or leg and said cast, said tube being closed at one end and open at the other end;

a considerable length of said elongate tube at said open end having a uniform, smooth inside relaxed diameter smaller than the diameter of that portion of said arm or leg over which said uniform diameter portion of said tube is adapted to extend, said uniform diameter portion forming a sealing portion of adjustable length;

a resilient, solid ring having greater thickness than said tube formed at the open end of said elongate tube, said ring forming a base structure for a roll of said uniform diameter portion and being adapted to be rolled along said arm or leg to a selected longitudinal position a substantial distance above the cast but below the end of the limb, the size and position of said roll depending upon the length of said limb and said cast;

said uniform diameter portion being of sufficient length that said roll is within the length of said uniform diameter portion for the entire range of limb and cast sizes on which it is adapted to be used, said ring being adapted to resiliently bias said uniform diameter portion at the location of said roll tightly against said arm or leg to seal the open end of said tube at any of its adjusted lengths; and a portion at the closed end of a shape different from said uniform diameter portion and of a shape and size to accommodate the hand or foot of the user.

2. A unitary, flexible covering to seal a cast on an individual's leg and adapted to accommodate legs and casts of a considerable range of lengths, comprising:

an elongate tube of resilient material for receiving said leg and said cast, said tube being closed at one end and open at the other end;

a considerable length of said elongate tube at said open end having a uniform, smooth inside relaxed diameter smaller than the diameter of that portion of said leg over which said uniform diameter portion of said tube is adapted to extend, said uniform diameter portion forming a sealing portion of adjustable length;

a resilient, solid ring having greater thickness than said tube formed at the open end of said elongate tube, said ring forming a base structure for a roll of said uniform diameter portion and being adapted to be rolled along said leg to a selected longitudinal position a substantial distance above the cast but below the end of the leg, the size and position of said roll depending upon the length of said leg and said cast;

said uniform diameter portion being of sufficient length that said roll is within the length of said uniform diameter portion for the entire range of leg and cast sizes on which it is adapted to be used, said ring being adapted to resiliently bias said uniform diameter portion at the location of said roll tightly against said leg to seal the open end of said tube at any of its adjusted lengths; and a portion at the closed end disposed at an angle relative to said uniform diameter portion and of a shape and size generally like that of a human foot.

3. A unitary, flexible covering to seal a cast on an individual's arm or leg from water in bathing comprising:

an elongate tube of resilient material for receiving said arm or leg and said cast, said tube being closed at one end and open at the other end;

said tube being of sufficient length to cover a cast on the arm or leg and for its open end to extend above said cast;

a portion of said elongate tube at said open end having a relaxed diamter smaller than the diameter of that portion of said arm or leg above the cast to form a seal above the cast; and a portion at the closed end of a larger diameter than said open end portion and of a shape and size to accommodate the hand or foot of the user without stretching.

4. A unitary flexible covering to seal a cast on an individual's leg from water in bathing, comprising:

an elongate tube of resilient material for receiving said leg and said cast, said tube being closed at one end and open at the other end and being of a length sufficient to extend up the leg above a cast on the leg or ankle;

a portion of said elongate tube at said open end having a relaxed diameter smaller than the diameter of that portion of said leg over which said open end of said tube is adapted to extend to a seal against the leg above the cast;

a portion at the closed end disposed at an angle relative to the remainder of said tube and of a shape and size generally like that of a human foot.

* * * * *